United States Patent
Charrad et al.

(10) Patent No.: US 9,916,417 B2
(45) Date of Patent: Mar. 13, 2018

(54) METHODS, APPARATUSES, SYSTEMS AND COMPUTER READABLE MEDIUMS FOR CONNECTING APPLICATIONS AND TOOLS WITHIN MEDICAL TASKFLOWS

(71) Applicant: Siemens Aktiengesellschaft, Munich (DE)

(72) Inventors: Chiheb Charrad, Neunkirchen A. Brand (DE); Lutz Dominick, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 323 days.

(21) Appl. No.: 13/798,753

(22) Filed: Mar. 13, 2013

(65) Prior Publication Data

US 2014/0278452 A1  Sep. 18, 2014

(51) Int. Cl.
| | | |
|---|---|---|
| G06Q 50/22 | (2012.01) | |
| G06Q 50/24 | (2012.01) | |
| G06F 19/00 | (2018.01) | |

(52) U.S. Cl.
CPC ......... *G06F 19/321* (2013.01); *G06F 19/327* (2013.01)

(58) Field of Classification Search
CPC ............... G06F 19/3487; G06F 19/345; G06F 17/30309; G06Q 50/22; G06Q 10/10; G06Q 50/24; G06Q 10/06
See application file for complete search history.

(56) References Cited

U.S. PATENT DOCUMENTS

| | | | |
|---|---|---|---|
| 2008/0141250 A1* | 6/2008 | Dorn et al. | 718/100 |
| 2011/0010192 A1* | 1/2011 | Backhaus et al. | 705/2 |
| 2013/0021337 A1 | 1/2013 | Blum et al. | |

OTHER PUBLICATIONS

Chinese Office Action dated Dec. 26, 2016 in Chinese Application No. 2014100763101, with English translation.

* cited by examiner

*Primary Examiner* — Maroun Kanaan
(74) *Attorney, Agent, or Firm* — Harness, Dickey & Pierce, P.L.C.

(57) ABSTRACT

A medical image evaluation and diagnosis system to dynamically connect clinical tools, clinical applications and clinical findings includes a work context auto alignment manager (WAALM). The WAALM extracts, from a clinical application and tool initiation request, clinical application and tool information for a first clinical taskflow, and connects, with at least a first clinical application initiated in response to the clinical application and tool initiation request, at least a first clinical tool based on the extracted clinical application and tool information, the first clinical tool being independent of the first clinical application.

49 Claims, 7 Drawing Sheets

| Amalgam Types |
|---|
| 2D |
| 3D |
| Pos |

TAB1

| Application-to-Context | |
|---|---|
| BasicReading | Context2D |
| BasicReading | ContextPos |
| PETCTBasic | Context3D |
| PETCTBasic | ContextPos |

TAB2

| Amalgam-to-Context-w/-Impl-Type | | |
|---|---|---|
| AmalType2D | Context2D_impl-v1 | |
| AmalTypePos | ContextPos-impl-v2 | |
| AmalType3D | Context3D_impl-v1 | |

TAB3

| Findings-to-Context | | |
|---|---|---|
| Find-1 | 2D-AmalType2D-Linetool | |
| Find-2 | 2D-AmalType2D-Circletool | |
| Find-3 | 2D-AmalType2D-Angletool | |

TAB4

| Tools-to-Context-w/ impl-type | |
|---|---|
| Linetool | Context2D-impl-v3 |
| Circletool | Context2D-impl-v1 |
| Angletool | Context2D-impl-v3 |
| ROItool3D | Context3D-impl-v1 |

TAB5

METHODS, APPARATUSES, SYSTEMS AND COMPUTER READABLE MEDIUMS FOR CONNECTING APPLICATIONS AND TOOLS WITHIN MEDICAL TASKFLOWS

BACKGROUND

Medical systems offer a relatively large number of complex applications for reading medical images. These complex applications are often distinguished with regard to standard routine reading and advanced reading. Conventionally, applications use flexible architecture approaches for balancing technical aspects and clinical needs with user demands. However, these technical solutions were solely 'inside application' approaches, which lead to a relatively large number of reading applications to map the traditional structure of clinical organizations, treatment, physiology, etc. to application scopes and architectures.

Although applications offer some commonalities in terms of tools and/or features between modalities, -ologies, across diseases, etc., the commonalities are limited. Quite often the user must switch to a different application or even a different taskflow to access necessary tools. In so doing, all or substantially all previously created findings are lost and must be re-created in the new taskflow. Some findings are preserved by utilizing a separate adhoc application offering more tools. But, this added adhoc application cannot be replaced nor can another adhoc application be added without switching to another taskflow. And, if the taskflow is again switched, all or substantially all previously created findings are again lost.

Additionally, for adding adhoc applications, the compatibility repository of, for example, syngo.via contained a white list of allowed applications, from where only a single application can be added and maintained without changing taskflows and losing findings generated in connection with the current taskflow.

SUMMARY

Example embodiments provide a WAALM component that learns the flow of user interaction by collecting intermediate results (e.g., findings) and information regarding how the findings were generated (e.g., with what tools) based on the amalgams. The amalgams form a new type of 'contract' between applications and tools (with or without findings).

The 'contract', for example, may include a rule that the technical coupling between application and tools is realized with a dedicated amalgam in between, which connects the application with the tool.

Another such rule may require that each amalgam is independent of both the application and the tool, so the amalgam is neither a part of the application nor of the tool. An amalgam entity is used to capture the run-time state regarding what applications and what tools have been connected. Amalgam entities are persisted and/or stored in a repository, which allows the WAALM infrastructure to recreate these connections between applications and tools such that the same tool connects to a new application using the same persistent amalgam entity.

Another such example 'contract' rule may require that the application identifies a default tool set that is shown by an application to the user after start-up. In this example, the start of such tools is handled by the WAALM that connects the tools to the application. In addition to the default tools, the WAALM may also start additional tools not included in the default tool set, for example, if such additional tools are required to show findings, or if the user has personalized the application in a way that he wants additional tools to be shown at start-up.

In example embodiments, the WAALM intercepts operations on data, applications, tools, and findings and stores the information in amalgams. Amalgams are then used later to restore, for example, findings in a different application context and adapt tools to this context using amalgams.

In connection with one or more example embodiments, the user can choose from more tools in a given clinical context with previous findings preserved, even when switching between different taskflows and/or applications.

When developing taskflows and applications, the set of available tools to choose from is no longer restricted during development and/or customization time. Rather, the system is adaptable to a current user defined clinical context at run-time and is even able to offer a context dependent guidance based on the gathered knowledge. Overall, the number of tools and/or applications may be decreased, which reduces development complexity. Tools can be tested or validated outside of applications, which also reduces test complexity.

At least one example embodiment provides a method for dynamically connecting clinical tools, clinical applications and clinical findings in a medical image evaluation and diagnosis system. According to at least this example embodiment, the method includes: extracting, from a clinical application and tool initiation request, clinical application and tool information for a first clinical taskflow; and connecting, with at least a first clinical application initiated in response to the clinical application and tool initiation request, at least a first clinical tool based on the extracted clinical application and tool information, the first clinical tool being independent of the first clinical application.

At least one other example embodiment provides a medical image evaluation and diagnosis system to dynamically connect clinical tools, clinical applications and clinical findings. According to at least this example embodiment, the system includes: a work context auto alignment manager to extract, from a clinical application and tool initiation request, clinical application and tool information for a first clinical taskflow, and to connect, with at least a first clinical application initiated in response to the clinical application and tool initiation request, at least a first clinical tool based on the extracted clinical application and tool information, the first clinical tool being independent of the first clinical application.

At least one other example embodiment provides a computer readable medium storing computer executable instructions that, when executed, cause a computer to perform a method for dynamically connecting clinical tools, clinical applications and clinical findings in a medical image evaluation and diagnosis system. According to at least this example embodiment, the method includes: extracting, from a clinical application and tool initiation request, clinical application and tool information for a first clinical taskflow; and connecting, with at least a first clinical application initiated in response to the clinical application and tool initiation request, at least a first clinical tool based on the extracted clinical application and tool information, the first clinical tool being independent of the first clinical application.

BRIEF DESCRIPTION OF THE DRAWINGS

In the detailed description of example embodiments given herein below and the accompanying drawings, like elements are represented by like reference numerals, which are given by way of illustration only and thus are not limiting of example embodiments and wherein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EMBODIMENTS

While example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium. A processor(s) will perform the necessary tasks.

Specific structural and functional details disclosed herein are merely representative for purposes of describing example embodiments of the present invention. Example embodiments may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, for example, those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art.

In the following description, illustrative embodiments will be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing clinical environments. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

Although example embodiments are described with regard to a computed tomography system, example embodiments are not limited thereto. For example, a system of an example embodiment of the present application may be another type of imaging system (e.g., MRI, PET, etc.).

Alternative embodiments of the invention may be implemented as a computer program product for use with a computer system, the processor program product being, for example, a series of processor instructions, code segments or program segments stored on a tangible or non-transitory data recording medium (processor readable medium), such as a diskette, CD-ROM, ROM, or fixed disk. The series of processor instructions, code segments or program segments can constitute all or part of the functionality of the methods of example embodiments described above, and may also be stored in any memory device, volatile or non-volatile, such as semiconductor, magnetic, optical or other memory device.

In some clinical environments (e.g., syngo.via), individual software-application building blocks (e.g., tasks) and sequence of tasks are configured, and these individual software application elements are processed by a user in the defined sequence. A sequence of tasks is referred to as a taskflow. Taskflows (e.g., a reading taskflow) define both positions of tasks and the data links between the tasks. The data links ensure that the output data of one task (or task function) is used as input data for a subsequent task. Tasks can typically be executed sequentially, in parallel, or in an arbitrary sequence.

Example embodiments provide methods, apparatuses, systems and computer readable storage mediums enabling more efficient and reliable automation of user interaction across workflows and/or across independent applications.

Figure 1:
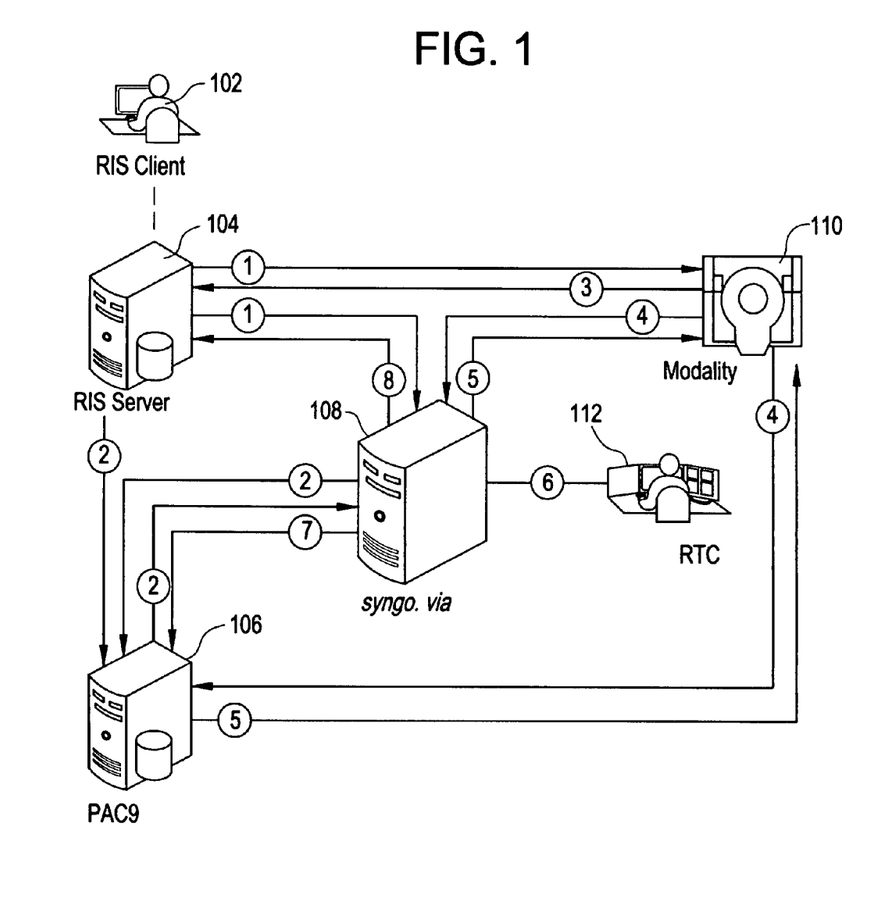
FIG. 1 illustrates a syngo architecture in which example embodiments may be implemented.

FIG. 1 illustrates a syngo architecture in which example embodiments may be implemented. The syngo architecture will be described with regard to the signal/message/communication flow diagram shown in FIG. 1. Because the components of the syngo architecture themselves are generally well-known, a more detailed discussion of each component is omitted. Although example embodiments will be described with regard to a syngo architecture, example embodiments should not be limited to only this example implementation.

Referring to FIG. 1, at (1) a clinical Radiology Information System (RIS) server 104 schedules a patient for a scan (e.g., computed tomography (CT), magnetic resonance imaging (MRI), x-ray, etc.) by sending a worklist to a modality 110. In one example, the RIS server 104 schedules a CT scan on a CT modality by sending the worklist to the modality 110. The RIS server 104 also sends the worklist to a syngo.via server 108 to inform the syngo.via server 108 about the scan work item, which may contain multiple scan series over a couple of visits. The RIS server 104 is accessible via a RIS client 102.

At (2), the RIS server 104 and/or the syngo.via server 108 prefetches prior studies for the patient of interest from a picture archiving and communication system (PACS) server 106. The prior studies may include prior findings to be compared against the current scan as well as the findings in the current scan.

At (3), in response to the worklist, the modality 110 sends procedure information (e.g., treatment details for accounting) to the RIS server 104.

At (4), after obtaining relevant images, the modality 110 sends the obtained images for the patient of interest to the syngo.via server 108 for creation of findings and comparison to prior findings. Also at (4), the modality 110 sends the obtained images to the PACS server 106 for archiving.

At (5), the syngo.via server 108 informs the modality 110 that all data for the patient of interest has been archived. In response, the modality 110 may then delete that data on the modality machines.

At (6), a clinical user (e.g., a clinical radiologist) accesses the obtained images archived at the syngo.via server 108 through a syngo.via client (RTC) terminal 112 to perform an image manipulation or reading activity and creates and/or edits findings on the images using tools and applications. The clinical user then summarizes the findings in a clinical report.

At (7), the syngo.via server 108 sends the clinical report to the PACS server 106. The PACS server 106 stores the clinical report upon receipt. Structured reporting of the report is also stored in the PACS server 116 (for archiving).

At (8), the syngo.via server 108 informs the RIS server 104 that the clinical user has signed-off on the report (e.g., for accounting).

The findings are created and reported, and may also be re-animated at the syngo.via server 108. The reading applications executed on the syngo.via server 108 show findings that are either newly created, or those that were created in prior studies.

Figure 7:
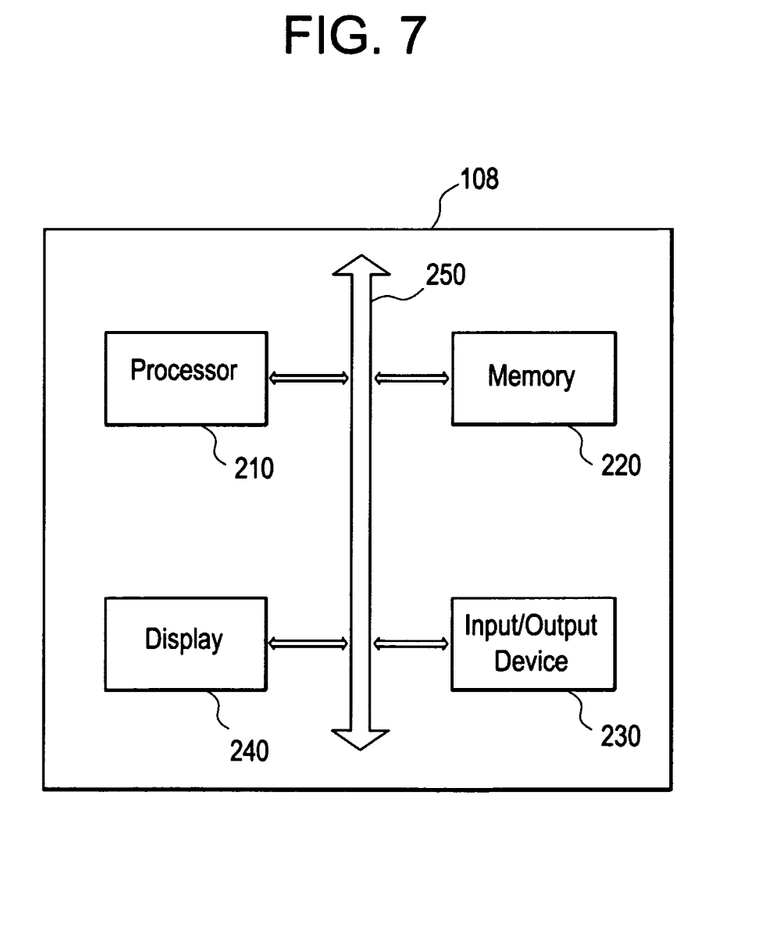
FIG. 7 illustrates an example embodiment of the server shown in FIG. 1.

FIG. 7 illustrates an example embodiment of the server 108 shown in FIG. 1.

Referring to FIG. 7, the server 108 includes a processor 210, an input/output device 230, a memory 220, a display 240, and a bus 250. The server 108 may be, for example, a personal computer configured for access by a clinical user via the workstation 112 shown in FIG. 1 to examine medical data.

The processor 210, input/output device 230, memory 220 and display 240 are configured to perform data communication with each other via the bus 250. Although the display 240 is shown as a component of the server 108, the display may be remotely located relative to the server 108. In this regard, the display 240 may refer to the display of the client workstation 112 in FIG. 1.

The processor 210 is configured to execute a program by accessing the memory 220 through the bus 250. The input/output device 230 is usable to input/output data to/from a user. The server 108 is capable of connecting to external devices (e.g., the workstation 112 in FIG. 1) by using the input/output device 230 and may exchange data with the external devices. The display 240 is configured to display a user interface based on commands received from a user of the client workstation 112 and/or commands received from the processor 210.

The memory 220 stores codes and/or programs for operation of the processor 210. For example, the memory 220 may include a data structure including instructions to execute the methods described herein. The memory 220 may store a user-interface container configured to host a patient browser and a plurality of imaging applications. Each of the applications may be independent and may be associated with the syngo architecture described in FIG. 1. The applications may be medical imaging applications which are designed according to the images created by the system of FIG. 1. Examples include a coronary image analysis application, a colon image analysis application, a cardio vascular application, a reading application, an image manipulation application, etc.

The memory 220 may include one or more memory modules. The memory modules may be separate physical memories (e.g., hard drives), separate partitions on a single physical memory and/or separate storage locations on a single partition of a single physical memory. The memory modules may store information associated with the installation of software (e.g., imaging processes).

It should be understood that a processor 210, such as a digital signal processor or a microcontroller, is specifically programmed to execute the instructions stored in the memory 220. For example, the processor 210 is specifically programmed to execute instructions stored in the memory 220 according to the example operations which are described in greater detail below.

Conventionally, tools for diagnosis of medical images, such as the tools used by the clinical user at the RTC terminal 112 in FIG. 1 are grouped into useful sets, and bundled within dedicated applications. The dedicated applications focus on, for example, organs (e.g., lung, heart, etc.), scanner plus organ (e.g., computed tomography (CT) head, magnetic resonance (MR) head, etc.), special scanner types for different "-ologies" (e.g., PET/CT oncology, cardiology, etc.), etc. These combinations address user demands and user perception, while also reducing complexity for the user. However, application developers/manufacturers cannot cover the demand for more combinations of tools while at the same time providing greater flexibility for each existing combination as desired by clinical users.

Example embodiments provide methods, apparatuses, systems and computer readable storage mediums that enable preservation of findings across taskflows and/or across independent applications. To preserve the findings, example embodiments utilize a work context auto-alignment manager (WAALM) and an associated knowledge repository (or database). For example purposes, the WAALM will be discussed as being implemented, and its functions executed, at the syngo.via server 108 shown in FIGS. 1 and 7. However, example embodiments are not limited to this implementation. In one alternative, the WAALM may be implemented, and its functions executed, at a client workstation or other computing device.

Figure 2:
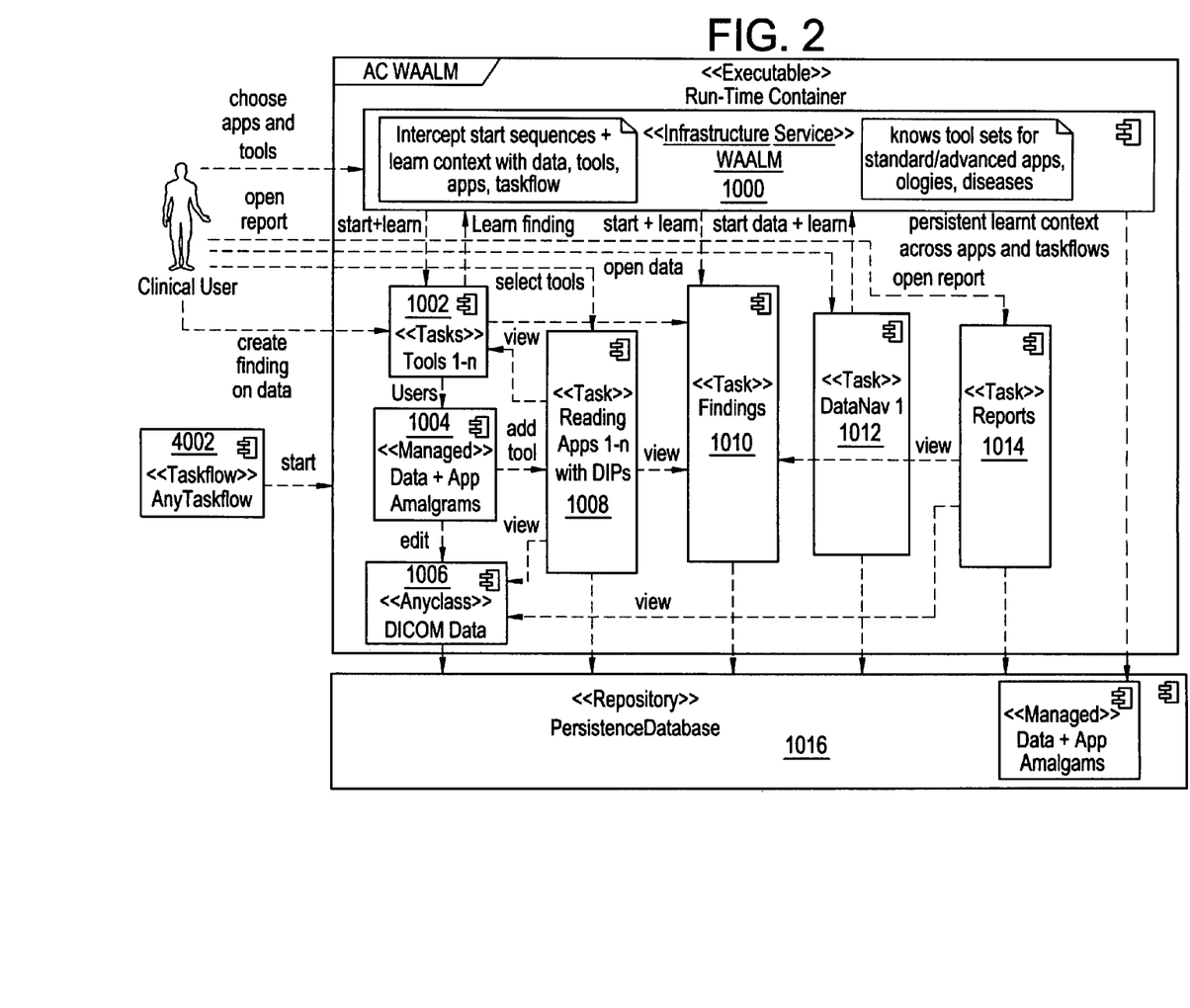
FIG. 2 illustrates a run-time container including a WAALM according to an example embodiment.

FIG. 2 illustrates a run-time container including a WAALM according to an example embodiment. The run-time container shown in FIG. 2 is an executable runtime container executable at the syngo.via server 108.

As shown in FIG. 2, the runtime container includes a plurality of tasks 1002, 1008, 1010, 1012, and 1014 associated with a reading taskflow, which defines a sequence of the plurality of tasks 1002, 1008, 1010, 1012, and 1014. As mentioned above, the taskflow defines both a position of each task and the data links between the tasks within the taskflow.

The runtime container shown in FIG. 2 also includes a WAALM 1000. According to at least this example embodiment, the WAALM 1000 collects the context of clinical user activities and uses context amalgam entities (also referred to herein as amalgams, amalgam entities, etc.) to manage applications and tools, initiate applications, and facilitate cooperation between applications and tools. The WAALM 1000 captures and stores knowledge about the current context of a taskflow and any new cooperation between applications and tools in the amalgams. The WAALM 1000 may be initiated by an explicit call (e.g., function or otherwise) or by intercepting life-cycle operations for applications, tools, findings, etc. Initiation or invocation of the WAALM 1000 results in creation and/or access of one or more amalgams, which are stored in a repository 1016. The repository 1016 is also referred to herein as a database, and will be discussed in more detail later.

A context amalgam entity or amalgam is a software component connecting applications with tools to be used within the applications.

Unlike a conventional application plug-in, amalgams do not merely connect to an application nor are they connected or bound to a particular application. Rather, amalgams connect 2 entities (e.g., arbitrary applications and tools). Except for application specific amalgams in which the application defines the application side interface, the amalgams define the application side interface.

The tool side interface is defined based on the tools and/or tool groups according to the intended amalgam type and the data to be processed. Accordingly, the findings created using the tools can be displayed in each application that is compatible with the tools used to create the findings.

One or more example embodiments change the relationship between applications and tools. Formerly, each application had an associated set of tools to which the application was limited. According to at least some example embodiments, however, tools and applications are provided on the same level, and cooperate on demand and upon user request. Thus, applications are no longer limited to an associated set of tools.

Figure 6:
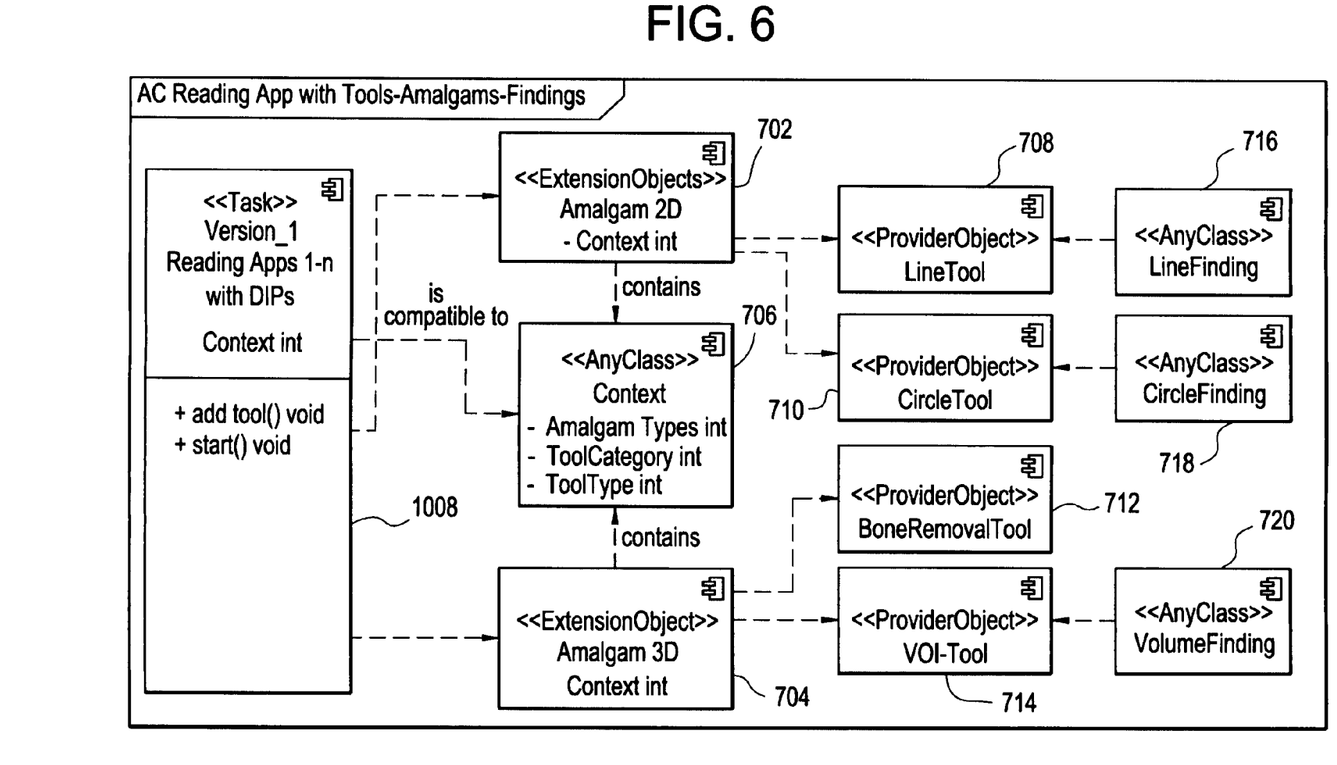
FIG. 6 is a block diagram illustrating example connections between tools, amalgams, findings, and the reading application task 1008 in FIG. 2.

FIG. 6 is a block diagram illustrating example connections between tools, amalgams, findings, and the reading application task 1008 in FIG. 2.

Referring to FIG. 6, the reading application task 1008 is associated with amalgams 702 and 704. In this example, the amalgam 702 is a 2D amalgam, whereas the amalgam 704 is a 3D amalgam. In this context, 2D and 3D refer to the tools associated with the given amalgam. However, as discussed in more detail below, each amalgam has a context that is multi-dimensional (e.g., two-dimensional) in nature.

Still referring to FIG. 6, each of the amalgams 702 and 704 has a context, which refers to the two-dimensional nature of the amalgam. For each amalgam, there is a context element with an associated state contained therein. In the example shown in FIG. 6, the context element is labeled "int", which is the name of the number type 'integer' on program code level. The label "int" is an example of a type that could be assigned to the parameters during software development.

The first of the two dimensions is the stateless implementation for connectivity of an application to one or more tools (referred to herein as the "stateless implementation for connectivity"). The stateless implementation for connectivity enables technical interfacing between application and tools. Such interfacing ensures connectivity at run-time such that calls and parameters are routed, for example, from the application to the tool. Because the domain driven interface designs of, for example, tools for 2D images have strong commonalities and rely on the identical data model for 2D data, only one or maybe only a few amalgams are needed for such a group of tools.

As shown in FIG. 6, the stateless implementation for connectivity of the 2D amalgam 702 connects the reading application 1008 with 2D tools 708 and 710. In this example, the 2D tools include a line tool 708 and a circle tool 710.

The stateless implementation for connectivity of the 3D amalgam 704 connects the reading application 1008 with 3D tools 712 and 714. In this example, the 3D tools include a bone removal tool 712 and a volume of interest (VOI) tool 714.

In a more specific example, if a clinical user is working within the reading application 1008, and wants to use the line tool 708 to create a finding on loaded data, the 2D amalgam 702 connects the reading application 1008 with the line tool 708 to enable the user to create the desired finding using the line tool 708.

In another example, if a clinical user is working within the reading application 1008, and wants to use the bone removal tool 712 to show/alter a prior finding on the loaded data, the 3D amalgam 704 connects the reading application 700 with the bone removal tool 712 needed to show/alter the existing finding.

The second of the two dimensions of an amalgam is referred to as "context stateful information." The context stateful information enables parameterization of the (same or a different) amalgam implementation later on, which (re)connects an application to tools based on the above-described stateless implementation for connectivity. Such context stateful information (also referred to herein as 'state') is persisted or stored in the repository or database 1016.

Referring back to FIG. 6, each of the amalgams 702 and 704 includes/contains context stateful information 706. The context stateful information 706 includes information identifying the tool (e.g., by category and/or type) and amalgam type associated with the tool utilized to create a given finding. According to at least some example embodiments, a tool is used to create a finding, and an amalgam is used to capture the 'state'; that is, what finding was created with what tool. In one example, as shown in FIG. 6, the "context stateful information" for a finding may include at least: tool category ToolCategory, amalgam implementation type AmalgamType (at creation time), and tool type ToolType for creation of the finding. The context stateful information is stored together with the findings in the repository 1016, which will be discussed in more detail below.

According to at least some example embodiments, more information is available to identify the data on which the findings were created. In a syngo.via system, such information is stored along with the findings. Alternatively, however, such information (e.g., UIDs (unique identifiers)) may be captured and stored within (or inside) the amalgam because findings are valid only for that particular data set of medical images on which the findings have been created.

According to at least some example embodiments, the findings or tools themselves need not store all necessary information for re-animation in arbitrary applications. If the clinical user switches from one application to another different application, then the application context changes while the clinical context (e.g., in terms of patient, study, images, findings, etc.) remains the same.

The term 'clinical context' refers to a situation in which the clinical user has a clinical study on the screen and performs some clinical workflow steps with an arbitrary number of interactions with a user interface (e.g., for 'reading' images to create the findings for the final diagnosis).

The term 'application context' refers to the application being used in connection with the current taskflow, which is part of the overall clinical workflow.

The DICOM standard (e.g., as used by RIS, PACS, Modality, syngo.via, etc.) covers the first part of this clinical data context (e.g., patient, study, series, images, etc.), but not the parameters, attributes, etc. that connect applications with arbitrary tools used to create findings.

In one example, tools may be categorized in terms of the number of dimensions (e.g., 2D, 3D, 4D), positioning, common, modus, etc., such that tool types associated with a single amalgam type are grouped together. In this regard, an amalgam type is an indication that an amalgam of that type is at least compatible with 1-n tool categories.

According to at least some example embodiments, the WAALM organizes tools by intent, rather than application, so that the tools are usable in connection with multiple different applications. The applications host arbitrary (or generic) tools or tool sets, which are mainly tools for image manipulation and findings creation/editing.

In one example, applications are accompanied by a description of the default tools to be loaded at start-up time. These tool lists may be configured in, for example, XML files and are presented at the time the application is installed. A user may install more tools and/or use an add-in-manager (or the like) to connect additional tools to the loaded application.

In accordance with at least some example embodiments, tools are not related to application implementation details, but rather to data, the findings based on the data, and the tool's capabilities (e.g., display capabilities). Similarly, findings are related to data and tools, not application implementation details.

According to at least one example embodiment, an amalgam identifies a dedicated connection type (with or without additional implementation), and connects at least two of the above entities (e.g., findings, data and/or tools) on demand, such that the entities are independent of the cooperating partners. Thus, one amalgam connection type may occur multiple times to serve different tools.

Referring back to FIG. 2, the WAALM 1000 enables the use of arbitrary tools within multiple applications on demand. The WAALM 1000 also organizes the compatibility between tools and applications using the repository 1016 with the current set of amalgams. Findings are preserved by being loaded and/or re-loaded together with their associated tools in a given application context, and the WAALM 1000 applies the old, new, or no amalgams.

Figure 3:
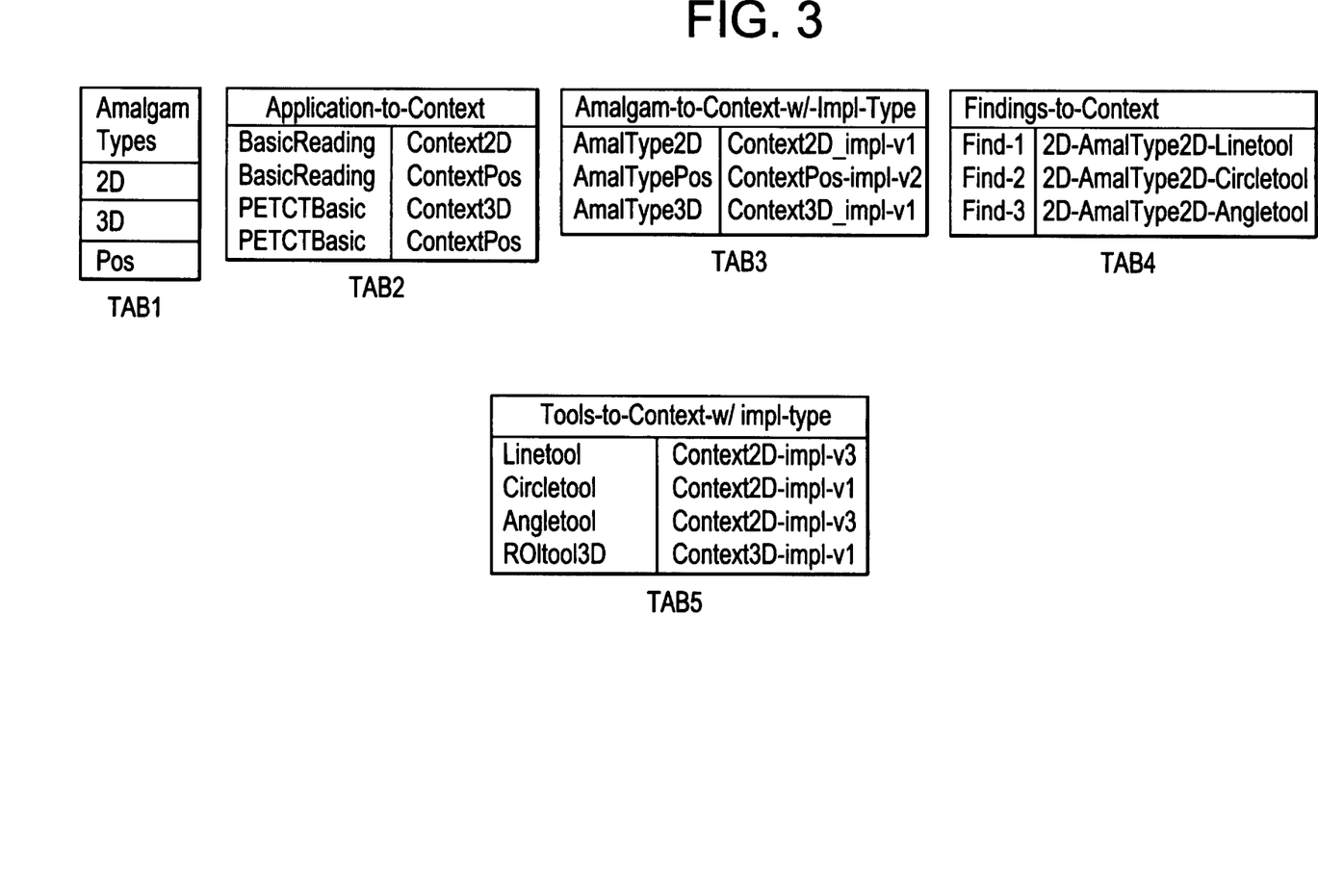
FIG. 3 illustrates an example of the repository 1016 shown in FIG. 2.

FIG. 3 illustrates an example of the repository 1016 shown in FIG. 2.

Referring to FIG. 3, the structure of the repository 1016 includes a plurality of tables TAB1 through TAB5, each of which will be discussed in more detail below. The repository 1016 associates amalgams, applications, tools and findings using context elements inside each amalgam. In one example, amalgams, applications, tools and findings are associated by storing amalgams in association with application identifiers, clinical tool identifiers (e.g., pointers, etc.) and clinical findings (or pointers to clinical findings) within the repository 1016.

The repository 1016 may be, for example, a local database system or a cloud based data storage service. The repository 1016 persists or stores amalgams (e.g., concrete amalgam entities from the run-time processes, which contain the context stateful information discussed above) and conventional database search index information to enable fast search functionality. The search index may include information about the amalgam types in the database, UIDs of the medical image data sets that currently have their amalgams in the repository, etc. The persisted amalgam entity includes, for example as shown in FIGS. 3 and 6, metadata (e.g., information such as, names, enumeration values, type names, entity identifiers, etc.) about the amalgam itself and also, for example, the tool name, the tool type and the concrete finding name, for which the amalgam entity was created.

The tools themselves are plug-ins with compiled code stored on the hard disk, and the findings themselves are stored in the medical database of, for example, the syngo.via system. The amalgam repository 1016 stores the amalgam entities and these 'point to' other types of entities (e.g., tools, findings, etc.) in other databases or storage repositories.

In the example shown in FIG. 3, configuration data is stored up-front (e.g., during installation of the application). The configuration data may identify tool categories, compatibilities between applications and amalgam types/categories, etc.

At development time, compatibility between tools and amalgam types is also defined such that the WAALM is able to connect tools and applications with the same amalgam types.

For example, each tool and application is associated with at least one amalgam type, and any tool and application having the same amalgam type may be connected together. In this regard, within a particular application, the clinical user may utilize any tool having the same amalgam type as that application.

With regard to FIG. 3, for example, table TAB1 stores categories both for tools and amalgams, which are connected in a compatible way. Table TAB1 organizes both the amalgams and how applications are compatible with amalgams.

Example amalgam types/categories include 'Null-Implementation-Type' (which is always supported), '2D', '3D', 'n-D', 'positioning', etc. But, example embodiments are not limited to these examples. As shown in FIG. 3, amalgam categories 2D, 3D, and Pos are stored in table TAB1.

Table TAB2 is indicative of the amalgams with which each application is compatible using the context element for each amalgam. In this example, the context element for the 2D amalgam is Context2D, the context element for the 3D amalgam is Context3D, and the context element for the Pos amalgam is ContextPos.

In table TAB2 the left column is a logical application name (clinical application identifier), and the right column identifies a compatibility for the applications. For the BasicReading application, for example, the right column declares compatibility to the above identifier 'Context2D'. So, the BasicReading can be re-staffed with everything inside Context2D. If another application declares compatibility to amalgam type or category 2D, then this other application can be re-staffed with everything from Context2D. The 'Context' (e.g., also 706 in FIG. 6) functions as a proxy of the situation where the application was in when the findings were created.

Similarly, for the PETCTBasic application, the right column declares compatibility to the above identifier 'Context3D'. So, the PETCTBasic application can be re-staffed with everything inside Context3D.

In table TAB3, the left column includes actual amalgam type names (e.g., AmalType2D, AmalTypePos, AmalType3D). The name AmalType2D, for example, means that there is an amalgam type for amalgam category 2D persisted in the repository 1016 (e.g., like 702 in FIG. 6). The right column in table TAB3 denotes that there is a concrete persisted amalgam instance with a context identifier (e.g., Context2D, ContextPos, Context3D, etc.), which matches an amalgam implementation of a given version (e.g., 'v1', 'v2', 'v3', etc.) of the amalgam type 2D. This identifier 'Context2D' is used to glue or tie things together.

Internal amalgam implementations (e.g., impl-v1, impl-v2, etc.) may, for example, connect the same tool to different application internals, if required. For example, internal amalgam implementations may forward mouse and keyboard events together with event specific data to tools.

Tables TAB2 and TAB3 provide compatibility between applications and amalgam types.

For example, tables TAB2 and TAB3 indicate that application BasicReading is compatible with AmalType2D. In this example, the context Context2D, which is the data object inside the amalgam, provides this compatibility connection.

Also at development time, the tools are defined with regard to the medical DICOM data from modalities (scanners) on which the tools can be used (e.g., ALL, 2D, 3D, CT images, MR images, etc.).

Amalgams are independent of medical DICOM data, but connect tools to the applications by regular function call forwarding so that the tools can use the data loaded into the application. This enables a clinical user to create a finding on the data within an application using any connected tool.

Referring back to the repository in FIG. 3, the left column in table TAB5 includes logical tool name (clinical tool identifier). Similar to table TAB3, the right column in table TAB5 denotes that there is a concrete persisted amalgam instance with a context identifier (e.g., Context2D, ContextPos, Context3D, etc.), which matches an amalgam implementation of a given version of the amalgam type. In the example shown in FIG. 3, each of the line tool Linetool and the circle tool Circletool in table TAB5 are connected to different internal implementations of context2D; that is, impl-v3 and impl-v1, respectively.

Returning to FIG. 2, as a clinical user creates findings using a tool within a particular application, the WAALM 1000 stores the created findings together with the data and tool from which the findings originated in the repository 1016. In one example, the WAALM 1000 stores the findings together with the data and tool in the form of a finding amalgam entity. Table TAB4 in FIG. 3 shows an example of a finding amalgam entity. The finding amalgam entity enables the findings to be re-animated after switching between taskflows, for example.

In more detail, table TAB4 contains the concrete findings (or pointer to the concrete findings, which is referred to herein as clinical findings identifier) in the left column and link information in the form of compound notation in the right column. In one example shown in FIG. 3, the findings denoted Find-1 in the left column are linked to three things in the compound notation 2D-AmalType2D-Linetool. The notation 2D-AmalType2D-Linetool indicates that the findings Find-1 are linked to the Context2D identifier (2D), the AmalgamType2D in table TAB3, and the tool Linetool, which is the tool used to generate the finding.

According to at least some example embodiments, tools become independent of the applications, which allows generalized interfacing between tools, amalgams and findings, and such interfaces with little or no medical semantics (e.g., execute( ), start( ), end( ), initialize( ), calls) remain backward compatible and relatively stable over time.

According to at least some example embodiments, the WAALM is configured to establish Application-to-Tool connections and read fitting amalgams from the repository or from the hard disk. The WAALM searches for amalgams that fit with the data that is loaded and that have an amalgam type/category supported by the application.

FIG. 2 is an application view with example applications from a clinical workflow and taskflow, saying that findings are created and maintained in Task 'Findings' (shows the findings only) and Task reading apps' (shows the images with their findings), and may be viewed by more apps. FIG. 2 along with the repository 1016 from FIG. 3 and the tables describe a simplified data base schema to exemplify an example organization of the database internally and the possibility of defining a database schema that will allow WAALM to store and precisely find the amalgams with tools and findings later on that match both with a given application plus the given data set to be loaded into that given application.

At least one example embodiment is directed to a method for dynamically connecting clinical tools, clinical applications and clinical findings in a medical image evaluation and diagnosis system. According to at least one example embodiment, the WAALM 1000 extracts clinical application and tool information for a first clinical taskflow from a clinical application and tool initiation request. The WAALM 1000 then connects at least a first clinical tool with at least a first clinical application based on the extracted clinical application and tool information. The first clinical tool is independent of the first clinical application, and the first clinical application is initiated in response to the clinical application and tool initiation request.

At least one other example embodiment provides a computer readable medium storing computer executable instructions that, when executed, cause a computer to perform a method for dynamically connecting clinical tools, clinical applications and clinical findings in a medical image evaluation and diagnosis system. According to this example embodiment, clinical application and tool information for a first clinical taskflow is extracted from a clinical application and tool initiation request; and at least a first clinical tool is connected with at least a first clinical application initiated in response to the clinical application and tool initiation request based on the extracted clinical application and tool information. The first clinical tool is independent of the first clinical application.

Figure 4:
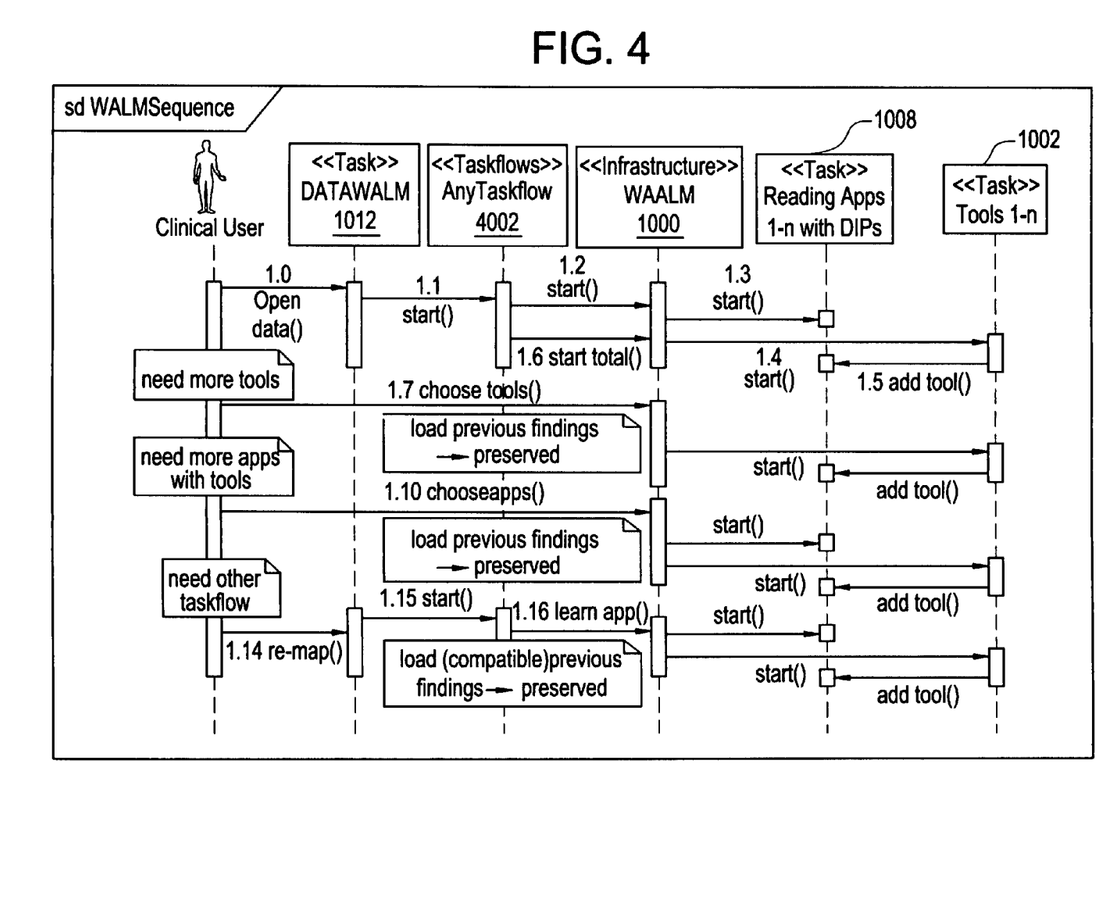
FIG. 4 is a flow diagram illustrating example interactions within the run time container shown in FIG. 2.
Figure 5:
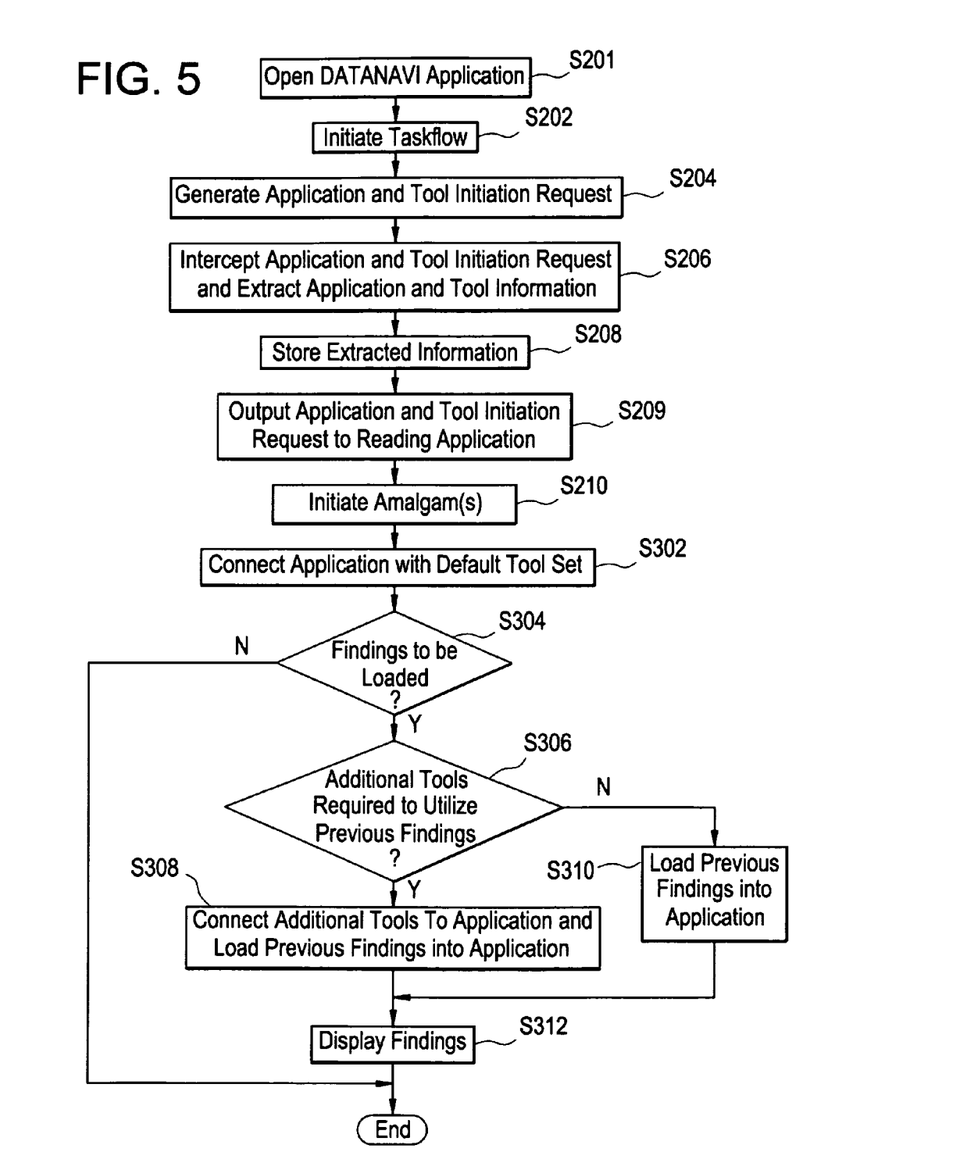
FIG. 5 is a flow chart illustrating a method according to an example embodiment.

FIG. 4 is a flow diagram illustrating example interactions within the run time container and the applications therein shown in FIG. 2. FIG. 5 is a flow chart illustrating a method according to an example embodiment.

Referring to FIGS. 2, 4 and 5, at S201 the user opens clinical data by initiating an open data( ) call 1.0 to the DataNavi application 1012. The DataNavi (or DataNavigator) application 1012 allows the clinical user to browse through a list of work items due for 'reading'. When the clinical user selects work items within the DataNavi application 1012, a workflow for reading (a.k.a. taskflow) 4002 with a set of applications is initiated or started. The set of applications show the images and offer tools to the clinical user to create findings for the data and to manipulate the image data itself (e.g., positioning, histograms, coloring, switch from 2D to 3D mode, etc.).

At S202, the DataNavi application 1012 initiates a mapped taskflow 4002 with a start( ) call 1.1. The mapped taskflow 4002 refers to the workflow type that can handle clinical data opened with the DataNavi application 1012.

At S204, the mapped taskflow 4002 attempts to initiate the reading application 1008 for use by the clinical user to evaluate the clinical data by generating an application and tool initiation request 1.2. In this example, the application and tool initiation request 1.2 may be a start( ) call intended for the reading application 1008. However, at S206, the WAALM 1000 intercepts the application and tool initiation request 1.2, and extracts application and tool information from the application and tool initiation request 1.2. The application and tool initiation request 1.2 includes applications to be started (e.g., BasicReading, PETCTBasic, etc.) and the tools to be used (e.g., Linetool, Circletool, Angletool, ROItool3D, etc.) to evaluate the clinical data.

At S208, the WAALM 1000 stores the extracted application and tool information in the repository 1016.

At S209, the WAALM 1000 outputs the application and tool initiation request 1.2 to the reading application 1008.

In addition to forwarding the application and tool initiation request 1.2, at S210 the WAALM 1000 initiates amalgams and tools 1.4 for the requested reading application based on the information extracted S206.

In more detail, at S206 the WAALM 1000 extracts from the application configuration (files or database) what tools (types and names) need to be loaded into the application by default, and creates the corresponding amalgam entities with which the application is compatible. Then, the WAALM 1000 extracts from the taskflow's input parameters what data has to be loaded into the same application and queries the repository 1016 for amalgams with findings for that data. The WAALM 1000 re-creates the amalgam run-time entities, reads the tools (types and names) from the amalgams, and merges the two tool sets (default and findings related). The WAALM 1000 checks, by reading the application's configuration, if all amalgams are compatible, and replaces incompatible amalgams with compatible ones. In this context compatible indicates that the application has the amalgam type in its compatibility list and the same amalgam is compatible to the tool required to show the finding. The WAALM 1000 removes remaining incompatible amalgams from the list.

The WAALM 1000 uses a configurable mechanism to intercept and potentially enrich the set of tools that are loaded at application start-up time. For example, such a mechanism may be a WAALM handler in the application's configuration, which instructs the WAALM 1000 to provide a list of tools to be loaded to the application, instead of the regular application handler that searched and provided the tools to the application. Instead of tools, the WAALM 1000 provides the merged list of amalgam entities to the application that in turn load tools that are compatible with the application. Other known mechanisms, such as code injection or placing a WAALM 'tool' in the application's tools folder on disk also exist.

At step S302, the WAALM 1000 connects the initiated application with a default set of tools at step S302 using the add tool( ) call 1.5. The default tool set may be defined in the application configuration at the time the application is developed. Alternatively, the default tool set and default set of amalgams for an application may be configured at run-time. In one example, the WAALM 1000 intercepts calls between applications and tools, identifies the amalgams types associated with the tools and applications, and uses the identified amalgams as the default set of amalgams. Each tool connects to the application (e.g., to become visible in the corner menus) using the add tool( ) call 1.5.

At step S304, the WAALM 1000 checks if there are previous findings associated with the current clinical context. I more detail, the WAALM 1000 extracts from the taskflow's input parameters what data has to be loaded into the same application and queries the repository 1016 for amalgams with findings for that data, re-creates the amalgam run-time entities, The mapped taskflow 4002 attempts to load the actual medical data with a data request 1.5. In this example, the data request from the mapped taskflow 4002 may be a start data( ) call. The WAALM 1000 intercepts the data request 1.5 by the mapped taskflow 4002, and extracts and/or examines information regarding of the type of medical data and the modality where the data was obtained.

At S306, the WAALM 1000 determines whether tools in addition to the tools in the default tool set are required to enable the user to utilize the findings (such that findings are not lost when the user re-opens a case in another, but compatible workflow). For example, the WAALM 1000 queries the repository 1016 for amalgams for the loaded data, and reads the findings and the tools (e.g., types and names) from such amalgams.

If the WAALM 1000 determines that additional tools are necessary to utilize the findings, then at S308 the WAALM 1000 connects the additional tools to the application in the manner described above. Also at step S308, the WAALM 1000 loads the previous findings identified at step S304 into the application. The previous findings are then available to the clinical user within the application, for example, by being displayed to the clinical user at S312. In one example, the previous findings may be displayed to the clinical user at the workstation 112 shown in FIG. 1.

Returning to step S306, if the WAALM 1000 determines that additional tools are not required to utilize the previous findings identified at step S304, then at S310 the WAALM 1000 loads the previous findings into the application using the default tool set, and displays the previous clinical findings to the clinical user at S312 so the previous findings are available to the clinical user within the application.

Returning to step S304, if the WAALM 1000 determines that there are no previous findings to be loaded in connection with the mapped taskflow 4002, then the application initiates with the default tool set and is available to the clinical user.

Referring back to FIG. 4, according to at least some example embodiments, when the user desires or needs to do so, the user is able to choose additional tools to be added to the reading application by initiating an add tools request 1.7. In this example, the add tools request may be a choose tools( ) call.

Within a particular application, the graphical user interface (GUI) may provide a 'more tools . . . ' selection or button, which enables the user to obtain tools in addition to those tool sets currently available within the application. Within the user interface, tool sets may be user specific, disease specific, -ology specific, organ specific, multi or single modality specific, based on external medical knowledge databases, etc.

In one example with regard to FIGS. 2, 4 and 5, the graphical user interface may provide a corner menu with a 'more . . . ' entry. A user click on the 'more . . . ' instructs the WAALM 1000 to search the repository for all tools compatible with the application and present the user the list for selection. In response to selection of one or more tools by the user, the WAALM 1000 adds an additional tool in the same or substantially the same manner as discussed above with regard to S302. Selected tools are inserted into the corner menus of the segments and can (optionally) extend into the default list of the application.

When the user selects the additional tools to be added to an application, the previous findings obtained with the previously loaded tools stay loaded and are preserved by the WAALM 1000.

According to at least some example embodiments, applications may have one or more application-specific sets of amalgams that work only for individual applications, but also fit with tools and corresponding findings as with the more general amalgams.

According to at least one example embodiment, a user may request more tools at run-time, and the WAALM may use the above matching criteria to offer only tools that fit both with data and the application. The user is also able to select additional tools from that list and create additional findings using these tools.

Example embodiments enable a user to add additional tools to a current taskflow without changing applications and/or losing previously loaded findings. The amalgams enable the user to do so because tools are no longer tied to applications. Rather, the tools are independent of the applications. Thus, the tools can essentially be loaded into applications on an ad-hoc basis.

Example embodiments also enable a user to add further applications into an existing taskflow while preserving previous findings obtained using the current application and tools associated therewith.

Referring again to FIGS. 2, 4 and 5, if the user desires to add another application ad-hoc into the mapped taskflow 4002, the user initiates an additional application request 1.10 to the WAALM 1000. In this example, the additional application request may be a choose apps( ) call. In response to the additional application request, the WAALM 1000 initiates the desired new application in the same or substantially the same manner as discussed above with regard to S302. In so doing, the existing findings from the previous application are preserved, and the WAALM 1000 also shows the findings created with the ad-hoc application.

Still referring to FIGS. 2, 4 and 5, if the user decides to switch between or re-map taskflows manually, then the first two applications and the original taskflow are discarded in response to a re-map( ) call 1.14. A start sequence 1.15, 1.16, 1.17 is then performed. The start sequence 1.15, 1.16, 1.17 is similar to the 1.1, 1.2 and 1.3, except that the findings created in the discarded taskflow are preserved and shown in the application initiated with regard to the second taskflow. Additionally, when the user initiates the second taskflow, the WAALM 1000 also adds tools necessary to show again all findings that have been created in the discarded taskflow.

At least one embodiment of the present application includes a computer readable medium. The computer readable medium includes code segments that, when executed by a processor cause the processor to intercept an application installation procedure, classify the application, determine information associated with the application and install the application based on the classification and the determined information. Installing the application may further include determining compatibility information of one or more target nodes and adding the application to at least one of the target nodes if the application compatibility information and the compatibility of the at least one target node is confirmed.

Although the above example was described with regard to a computed tomography system, example embodiments are not limited thereto. For example, system may be another imaging system (e.g., MRI, PET, etc.). Further, example embodiments are not limited to imaging systems. For example, example embodiments may be related to a clinical study system or other health care management system. Further, as one skilled in the art will appreciate, example embodiments may be related to any system using several cooperating applications such as manufacturing equipment (e.g., robots) or cloud computing environments, but are not limited thereto.

While example embodiments have been particularly shown and described, it will be understood by one of ordinary skill in the art that variations in form and detail may be made therein without departing from the spirit and scope of the claims. The invention being thus described, it will be obvious that the same may be varied in many ways. Such variations are not to be regarded as a departure from the invention, and all such modifications are intended to be included within the scope of the invention.

We claim:

1. A method for dynamically connecting clinical tools, clinical applications and clinical findings in a medical image evaluation and diagnosis system including a processor and a memory, the method comprising:
    intercepting, by a work context auto alignment manager executed on the processor, a clinical application and tool initiation request intended for at least a first clinical application, the clinical application and tool initiation request requesting initiation of at least the first clinical application, and identifying at least a first clinical tool to be used to evaluate medical images and identify diagnoses, the work context auto alignment manager being separate from the first clinical application;
    extracting, by the work context auto alignment manager, clinical application and tool information from the clinical application and tool initiation request, the clinical application and tool information being for a first clinical taskflow;
    first initiating, by the work context auto alignment manager, the first clinical application;
    second initiating, by the work context auto alignment manager, the first clinical tool, the second initiating being independent of the first initiating;
    connecting, by the work context auto alignment manager, the first clinical tool with the first clinical application based on the extracted clinical application and tool information, the first clinical tool being independent of the first clinical application; and
    generating first clinical findings using the first clinical tool connected to the first clinical application; wherein
        the first clinical application is a medical image evaluation and diagnosis application,
        the first clinical tool is a medical image evaluation and diagnosis tool providing functionality for manipulating medical images within the first clinical application,
        the clinical application and tool information identifies the medical image evaluation and diagnosis tool, and
        the first clinical findings are medical findings.

2. The method of claim 1, further comprising:
    loading, into the first clinical application, prior clinical findings created using the first clinical tool.

3. The method of claim 2, wherein the prior clinical findings are created within a previous clinical taskflow.

4. The method of claim 1, wherein the first clinical tool is connected with the first clinical application at runtime of the first clinical application.

5. The method of claim 1, wherein
    the first initiating initiates the first clinical application in response to the clinical application and tool initiation request.

6. The method of claim 1, further comprising:
    storing the first clinical findings in association with a first clinical application identifier and a first clinical tool identifier to connect the first clinical application with the first clinical tool and the first clinical findings.

7. The method of claim 6, further comprising:
    initiating at least a second clinical application;
    connecting the second clinical application with the first clinical tool; and
    displaying the first clinical findings within the second clinical application using the first clinical tool.

8. The method of claim 1, further comprising:
    connecting a second clinical tool with the first clinical application;
    creating second clinical findings using the second clinical tool; and
    displaying the first clinical findings and the second clinical findings within the second clinical application.

9. The method of claim 1, further comprising:
    switching from the first clinical taskflow to a second clinical taskflow; and
    displaying the first clinical findings within the second clinical taskflow.

10. The method of claim 1, further comprising:
    connecting the first clinical application with a default tool set associated with the first clinical application.

11. The method of claim 10, wherein the first clinical tool is part of the default tool set.

12. The method of claim 1, further comprising:
    identifying clinical findings to be loaded into the first clinical application;
    determining whether additional clinical tools are required to utilize the clinical findings within the first clinical application; and
    loading the clinical findings into the first clinical application if additional clinical tools are not required to utilize the clinical findings within the first clinical application.

13. The method of claim 1, further comprising:
    identifying clinical findings to be loaded into the first clinical application;
    determining whether additional clinical tools are required to utilize the clinical findings within the first clinical application;
    connecting, with the first clinical application, at least one second clinical tool to utilize the clinical findings if additional clinical tools are required to utilize the clinical findings within the first clinical application; and
    loading the clinical findings into the first clinical application.

14. The method of claim 13, further comprising:
    loading the clinical findings into the first clinical application if additional clinical tools are not required to utilize the clinical findings within the first clinical application.

15. The method of claim 1, wherein the connecting comprises:
    creating, in response to the clinical application and tool initiation request, a software component to connect the first clinical application with the first clinical tool; and
    storing, in a database, the software component in association with a first clinical application identifier and a first clinical tool identifier to connect the first clinical application with the first clinical tool.

16. The method of claim 15, wherein the connecting further comprises:
    accessing the database to connect the first clinical application with the first clinical tool in response to the clinical application and tool request.

17. A medical image evaluation and diagnosis system to dynamically connect clinical tools, clinical applications and clinical findings, the system comprising:
    a processor including a work context auto alignment manager to,
        intercept a clinical application and tool initiation request intended for at least a first clinical application, the clinical application and tool initiation request requesting initiation of at least the first clinical application, and identifying at least a first clinical tool to be used to evaluate medical images and identify diagnoses, the work context auto alignment manager being separate from the first clinical application,
        extract, from the clinical application and tool initiation request, clinical application and tool information for a first clinical taskflow,
        initiate the first clinical application,
        initiate the first clinical tool independent of the initiation of the first clinical application, and
        connect the first clinical tool with the first clinical application based on the extracted clinical application and tool information, the first clinical tool being independent of the first clinical application;
    wherein the processor is further configured to generate first clinical findings using the first clinical tool connected to the first clinical application;
    wherein the first clinical application is a medical image evaluation and diagnosis application;
    wherein the first clinical tool is a medical image evaluation and diagnosis tool providing functionality for manipulating medical images within the first clinical application;
    wherein the clinical application and tool information identifies the medical image evaluation and diagnosis tool; and
    wherein the first clinical findings are medical findings.

18. The system of claim 17, wherein the work context auto alignment manager is further configured to load, into the first clinical application, prior clinical findings created using the first clinical tool.

19. The system of claim 18, wherein the prior clinical findings are created within a previous clinical taskflow.

20. The system of claim 18, wherein the work context auto alignment manager is further configured to,
    initiate the first clinical application in response to the clinical application and tool initiation request.

21. The system of claim 17, wherein the first clinical tool is connected with the first clinical application at runtime of the first clinical application.

22. The system of claim 17, further comprising:
    a repository to store the first clinical findings in association with a first clinical application identifier and a first clinical tool identifier to connect the first clinical application with the first clinical tool and the first clinical findings.

23. The system of claim 22, wherein the work context auto alignment manager is further configured to initiate at least a second clinical application, and connect the second clinical application with the first clinical tool, and wherein the system further includes,
    a display to display the first clinical findings within the second clinical application using the first clinical tool.

24. The system of claim 17, wherein the work context auto alignment manager is further configured to connect a second clinical tool with the first clinical application, and create second clinical findings using the second clinical tool, and wherein the system further includes,
    a display to display the first clinical findings and the second clinical findings within the second clinical application.

25. The system of claim 17, wherein the system is configured to display the first clinical findings within the second clinical taskflow when a clinical user switches from the first clinical taskflow to a second clinical taskflow.

26. The system of claim 17, wherein the work context auto alignment manager is further configured to connect the first clinical application with a default tool set associated with the first clinical application.

27. The system of claim 26, wherein the first clinical tool is part of the default tool set.

28. The system of claim 17, wherein the work context auto alignment manager is further configured to,
    identify clinical findings to be loaded into the first clinical application,
    determine whether additional clinical tools are required to utilize the clinical findings within the first clinical application, and
    load the clinical findings into the first clinical application if additional clinical tools are not required to utilize the clinical findings within the first clinical application.

29. The system of claim 17, wherein the work context auto alignment manager is further configured to,
    identify clinical findings to be loaded into the first clinical application,
    determine whether additional clinical tools are required to utilize the clinical findings within the first clinical application,
    connect, with the first clinical application, at least one second clinical tool to utilize the clinical findings if additional clinical tools are required to utilize the clinical findings within the first clinical application, and
    load the clinical findings into the first clinical application.

30. The system of claim 29, wherein the work context auto alignment manager is further configured to,
    load the clinical findings into the first clinical application if additional clinical tools are not required to utilize the clinical findings within the first clinical application.

31. The system of claim 17, wherein the work context auto alignment manager is further configured to connect at least the first clinical tool with at least the first clinical application by,
    creating, in response to the clinical application and tool initiation request, a software component to connect the first clinical application with the first clinical tool, and
    storing, in a database, the software component in association with a first clinical application identifier and a first clinical tool identifier to connect the first clinical application with the first clinical tool.

32. The system of claim 31, wherein the work context auto alignment manager is further configured to,
  access the database to connect the first clinical application with the first clinical tool in response to the clinical application and tool request.

33. The medical image evaluation and diagnosis system of claim 17, wherein
  the work context auto alignment manager is configured to connect the first clinical tool with the first clinical application via an amalgam between the first clinical tool and the first clinical application;
  the amalgam is persistent and independent of the first clinical tool and the first clinical application, the amalgam being further configured to capture a run-time state indicative of the connection between the first clinical tool and the first clinical application; and
  the work context auto alignment manager is further configured to connect the first clinical tool with a second clinical application, and restore the first clinical findings in the second clinical application, based on the amalgam.

34. A non-transitory computer readable medium storing computer executable instructions that, when executed, cause a computer to perform a method for dynamically connecting clinical tools, clinical applications and clinical findings in a medical image evaluation and diagnosis system, the method comprising:
  intercepting, by a work context auto alignment manager executed on a processor, a clinical application and tool initiation request intended for at least a first clinical application, the clinical application and tool initiation request requesting initiation of at least the first clinical application, and identifying at least a first clinical tool to be used to evaluate medical images and identify diagnoses, the work context auto alignment manager being separate from the first clinical application;
  extracting, by the work context auto alignment manger, clinical application and tool information from the clinical application and tool initiation request, the clinical application and tool information being for a first clinical taskflow;
  first initiating the first clinical application;
  second initiating the first clinical tool, the second initiating being independent of the first initiating;
  connecting, by the work context auto alignment manger, the first clinical tool with at least the first clinical application based on the extracted clinical application and tool information, the first clinical tool being independent of the first clinical application; and
  generating first clinical findings using the first clinical tool connected to the first clinical application; wherein
    the first clinical application is a medical image evaluation and diagnosis application,
    the first clinical tool is a medical image evaluation and diagnosis tool providing functionality for manipulating medical images within the first clinical application,
    the clinical application and tool information identifies the medical image evaluation and diagnosis tool, and
    the first clinical findings are medical findings.

35. The computer readable medium of claim 34, wherein the method further comprises:
  loading, into the first clinical application, prior clinical findings created using the first clinical tool.

36. The computer readable medium of claim 34, wherein the first clinical tool is connected with the first clinical application at runtime of the first clinical application.

37. The computer readable medium of claim 34, wherein
  first initiating initiates the first clinical application in response to the clinical application and tool initiation request.

38. The computer readable medium of claim 35, wherein the prior clinical findings are created within a previous clinical taskflow.

39. The computer readable medium of claim 34, wherein the method further comprises:
  storing the first clinical findings in association with a first clinical application identifier and a first clinical tool identifier to connect the first clinical application with the first clinical tool and the first clinical findings.

40. The computer readable medium of claim 39, wherein the method further comprises:
  initiating at least a second clinical application;
  connecting the second clinical application with the first clinical tool; and
  displaying the first clinical findings within the second clinical application using the first clinical tool.

41. The computer readable medium of claim 34, wherein the method further comprises:
  connecting a second clinical tool with the first clinical application;
  creating second clinical findings using the second clinical tool; and
  displaying the first clinical findings and the second clinical findings within the second clinical application.

42. The computer readable medium of claim 34, wherein the method further comprises:
  switching from the first clinical taskflow to a second clinical taskflow; and
  displaying the first clinical findings within the second clinical taskflow.

43. The computer readable medium of claim 34, wherein the method further comprises:
  connecting the first clinical application with a default tool set associated with the first clinical application.

44. The computer readable medium of claim 43, wherein the first clinical tool is part of the default tool set.

45. The computer readable medium of claim 34, wherein the method further comprises:
  identifying clinical findings to be loaded into the first clinical application;
  determining whether additional clinical tools are required to utilize the clinical findings within the first clinical application; and
  loading the clinical findings into the first clinical application if additional clinical tools are not required to utilize the clinical findings within the first clinical application.

46. The computer readable medium of claim 34, wherein the method further comprises:
  identifying clinical findings to be loaded into the first clinical application;
  determining whether additional clinical tools are required to utilize the clinical findings within the first clinical application;
  connecting, with the first clinical application, at least one second clinical tool to utilize the clinical findings if additional clinical tools are required to utilize the clinical findings within the first clinical application; and
  loading the clinical findings into the first clinical application.

47. The computer readable medium of claim 46, wherein the method further comprises:

loading the clinical findings into the first clinical application if additional clinical tools are not required to utilize the clinical findings within the first clinical application.

48. The computer readable medium of claim 34, wherein the connecting comprises:
creating, in response to the clinical application and tool initiation request, a software component to connect the first clinical application with the first clinical tool; and
storing, in a database, the software component in association with a first clinical application identifier and a first clinical tool identifier to connect the first clinical application with the first clinical tool.

49. The computer readable medium of claim 48, wherein the connecting further comprises:
accessing the database to connect the first clinical application with the first clinical tool in response to the clinical application and tool request.

\* \* \* \* \*